(12) United States Patent
Marttila et al.

(10) Patent No.: US 8,696,571 B2
(45) Date of Patent: Apr. 15, 2014

(54) CONTINUITY CIRCUITS FOR DETECTING ACCESS DISCONNECTION

(71) Applicants: Baxter International Inc., Deerfield, IL (US); Baxter Healthcare S.A., Glattpark (CH)

(72) Inventors: Alan W. Marttila, Waukegan, IL (US); William W. Chan, Lake in the Hills, IL (US); Reema V. Bhavnani, Milwaukee, WI (US)

(73) Assignees: Baxter International Inc., Deerfiled, IL (US); Baxter Healthcare S.A., Glattpark (Opfikon) (CH)

( * ) Notice: Subject to any disclaimer, the term of this patent is extended or adjusted under 35 U.S.C. 154(b) by 1 day.

(21) Appl. No.: 13/741,015

(22) Filed: Jan. 14, 2013

(65) Prior Publication Data

US 2013/0123699 A1    May 16, 2013

Related U.S. Application Data

(63) Continuation of application No. 11/862,984, filed on Sep. 27, 2007, now Pat. No. 8,360,977.

(51) Int. Cl.
*A61B 5/00*    (2006.01)

(52) U.S. Cl.
USPC .......................... 600/371; 604/361

(58) Field of Classification Search
CPC ............... A61F 13/42; A61B 5/02042; A61M 2001/3656
USPC .................... 600/371; 604/361, 364
See application file for complete search history.

(56) References Cited

U.S. PATENT DOCUMENTS

| | | | |
|---|---|---|---|
| 4,193,068 A | | 3/1980 | Ziccardi |
| 4,499,214 A | * | 2/1985 | Sortwell ........................ 523/336 |
| 4,501,828 A | | 2/1985 | Hadermann et al. |
| 5,332,524 A | | 7/1994 | Kaylor |
| 5,411,857 A | | 5/1995 | Beaudenon et al. |
| 5,429,590 A | | 7/1995 | Saito et al. |
| 5,433,201 A | | 7/1995 | Manthey |

(Continued)

FOREIGN PATENT DOCUMENTS

WO    2006/008866    1/2006

OTHER PUBLICATIONS

International Search Report and Written Opinion issued Feb. 12, 2009 for corresponding Intl. Appln. No. PCT/US/2009/066101.

*Primary Examiner* — Navin Natnithithadha
*Assistant Examiner* — Eric Messersmith
(74) *Attorney, Agent, or Firm* — K&L Gates LLP

(57) ABSTRACT

A monitor for an extracorporeal therapy access site is disclosed. The monitor includes a bandage atop or adjacent the access site and a sensor for monitoring the bandage. The bandage includes a layer of polymer that expands when wetted with blood. The expansion causes a break in continuity of the sensor, or in an alternate embodiment, causes a sensor to cease detecting a target. When the break occurs, the control circuit monitoring the bandage sends a signal that a break has occurred, and a remote monitor then takes appropriate action, such as ceasing therapy, sending an alert, or sounding an alarm. In another embodiment, connecting wires in a continuity circuit are held apart by a polymer that dissolves when contacted by blood. If a leak occurs and a small portion of the polymer dissolves, the wires make contact, thus detecting a blood leak.

20 Claims, 8 Drawing Sheets

(56) References Cited

U.S. PATENT DOCUMENTS

| | | |
|---|---|---|
| 5,522,755 A | 6/1996 | Farrell et al. |
| 5,617,857 A | 4/1997 | Chader et al. |
| 5,817,076 A * | 10/1998 | Fard ................ 604/361 |
| 6,112,380 A | 9/2000 | Dolan et al. |
| 6,165,157 A | 12/2000 | Dillon et al. |
| 6,183,436 B1 | 2/2001 | Korteweg et al. |
| 6,332,089 B1 | 12/2001 | Acker et al. |
| 6,445,304 B1 | 9/2002 | Bandeian |
| 6,979,306 B2 | 12/2005 | Moll |
| 7,037,983 B2 | 5/2006 | Huang et al. |
| 7,147,615 B2 * | 12/2006 | Wariar et al. ........ 604/6.16 |
| 7,523,649 B2 | 4/2009 | Corey et al. |
| 2002/0198483 A1 | 12/2002 | Wariar et al. |
| 2003/0195454 A1 | 10/2003 | Wariar |
| 2004/0106722 A1 | 6/2004 | Haraguchi |
| 2004/0230172 A1 | 11/2004 | Shapira |
| 2005/0038325 A1 * | 2/2005 | Moll ................ 600/300 |
| 2006/0074369 A1 | 4/2006 | Oishi et al. |
| 2006/0197658 A1 | 9/2006 | Light et al. |
| 2007/0049822 A1 | 3/2007 | Bunce et al. |
| 2007/0275296 A1 | 11/2007 | Ueda et al. |
| 2008/0033383 A1 * | 2/2008 | Cantor et al. ........ 604/361 |
| 2008/0065006 A1 | 3/2008 | Roger |
| 2008/0195021 A1 | 8/2008 | Roger |
| 2008/0195060 A1 | 8/2008 | Roger |
| 2009/0079578 A1 | 3/2009 | Dvorsky |
| 2009/0080757 A1 | 3/2009 | Roger |
| 2009/0082646 A1 | 3/2009 | Bouton |
| 2009/0082647 A1 | 3/2009 | Busby |
| 2009/0082649 A1 | 3/2009 | Muller |
| 2009/0082653 A1 | 3/2009 | Rhode |
| 2009/0082676 A1 | 3/2009 | Bennison |
| 2009/0088612 A1 | 4/2009 | Bouton |
| 2009/0088683 A1 | 4/2009 | Roger |
| 2009/0105627 A1 | 4/2009 | Rhode |
| 2010/0022934 A1 | 1/2010 | Hogard |
| 2010/0022935 A1 | 1/2010 | Muller |

* cited by examiner

CONTINUITY CIRCUITS FOR DETECTING ACCESS DISCONNECTION

PRIORITY CLAIM

This application is a continuation application of, and claims the benefit of and priority to, U.S. patent application Ser. No. 11/862,984, filed on Sep. 27, 2007, the entire contents of which are incorporated herein by reference.

BACKGROUND

The invention is in the field of medical treatments generally and patient vascular access systems. The present invention relates to embodiments of a method and a system for detecting blood leakage during extracorporeal blood treatment or other medical procedure.

The maxim of "first, do no harm," may be a good summary of the Hippocratic oath required of doctors and practiced by medical professionals. Nowhere is this principle required more than in modern medicine. With patients living longer, there are more extended treatments and more frail patients than ever. Such patients are in danger from complications that can arise from continuing therapeutic procedures, and even from diagnostic procedures, that are necessary for their continued care. Treatments involving extra-corporeal blood treatment are clear examples.

The most obvious danger is infection, but the harm caused by infection can be overcome by not re-using even supposedly-sterile devices and by diligent attention by the patient himself or herself, and by care givers attending to the patient. Other dangers also arise, but, like infections, have been difficult to eradicate. One of these dangers arises in blood treatment procedures in which the blood of a patient is physically removed from the patient for treatment, and then returned, all in the same procedure. Removal and return of blood is practiced in hemodialysis, for those persons whose kidneys do not function well. Other procedures, such as apheresis, involve removing blood from a patient or a donor to separate blood platelets or plasma from the red blood cells and then returning the red blood cells to the patient or donor, as described in U.S. Pat. Nos. 5,427,695 and 6,071,421.

The extracorporeal medical treatments described above require that the blood be removed for treatment and then returned. This requires access to the patient's vascular system, from which blood is removed and to which blood is then returned. If a "batch" treatment is used, that is, a quantity of blood is withdrawn, treated and returned, only a single needle is used. Each batch of such treatment is typically short, and the treatment is attended by a medical professional at a clinic or hospital. A variation on the batch treatment is a "batch" continuous method in which only a single needle is used. There are distinct withdraw and return phases in a batch continuous process. During the draw phase, blood is processed and additional blood is sent to a holding container to be processed during the return phase. In the return phase, blood is processed from the holding container and then returned to the patient or donor through the single needle. Other treatments are continuous, such as the platelet separation discussed above, or dialysis treatment, and may require a duration of several hours or even overnight.

Continuous treatments require two needles, or access points, one for withdrawal of blood and one for return. The withdrawal site is normally an artery, and a needle and a pump are used to provide the blood to the therapeutic machine. It is relatively simple to detect a problem with drawal, for instance, if the withdrawal needle is dislodged, using conventional air sensor technology. Detecting a problem in the return of the blood to the patient is more difficult. The return line typically includes a needle with venous access. If the return line is dislodged, the blood is not returned to the patient's vascular system, but may continue to be pumped and may accumulate near the patient. Depending on the pumping rate of the blood and the time for treatment, this could have life-threatening effects on the patient within a very short period of time.

Accordingly, a number of apparatuses have been devised for detecting needle dislodgement, especially venous needle dislodgement. An example is U.S. Pat. Appl. Publ. 2006/0130591. In a device according to this application, a venous needle is equipped with a photosensor and is covered with an opaque patch. This device would not send a signal or an alarm if the needle begins leaking or is only slightly dislodged. For example, the photosensor could still fail to detect light because the needle has not been dislodged sufficiently to expose the photosensor to light. In addition, this method requires ambient light and would thus not be suitable for patients that cover their arm with a blanket or who perform nocturnal dialysis while sleeping in a dark bedroom.

Numerous other techniques have been devised, many of them depending on a flow of blood causing conductivity between two electrodes or two wires. What is needed is a better way of quickly detecting dislodgement of a venous or other needle from a patient, so that inadvertent loss of blood and harm to the patient is avoided.

SUMMARY

One embodiment is a method for detecting blood leakage. The method includes steps of furnishing a pad with an expandable polymer layer and a sensor, placing the pad near an access site for an extracorporeal blood therapy, taking an initial reading of the sensor, monitoring the access site by taking additional readings of the sensor during an extracorporeal blood processing therapy, and sending a signal if a reading of the sensor is consistent with expansion of the expandable polymer layer and a break of continuity of the sensor.

Another embodiment a method of detecting a fluid. The method includes steps of providing a fluid conveyor comprising at least one outer layer and a hydrophilic inner layer, the hydrophilic inner layer configured to wick blood, placing the fluid conveyor near an extracorporeal therapy access site, monitoring a sensor to detect a presence of blood in the fluid conveyor, and sending a signal to a monitoring circuit if blood is detected.

Another embodiment is an access disconnect detector. The access disconnect connector includes a pad having an expandable layer, and a detection circuit mounted near or atop the pad, wherein the pad is configured for placement adjacent an extracorporeal therapy access site, the expandable layer is configured for expanding upon contact with blood, and the detection circuit is configured for wireless communication with an extracorporeal therapy machine or a controller in communication with the extracorporeal therapy machine.

Another embodiment is an access disconnect detector. The access disconnect detector includes a fluid conveyor comprising at least one outer layer and a hydrophilic inner layer, the hydrophilic inner layer configured to wick blood away from an extracorporeal therapy access site, a detector for detecting the blood within the fluid conveyor, and a control circuit in operable communication with the detector, wherein the detector is configured to detect blood in the fluid conveyor and the control circuit is configured to send a signal to alert a user or a caregiver of a presence of blood.

Additional features and advantages are described herein, and will be apparent from, the following Detailed Description and the figures.

DETAILED DESCRIPTION

Figure 1:
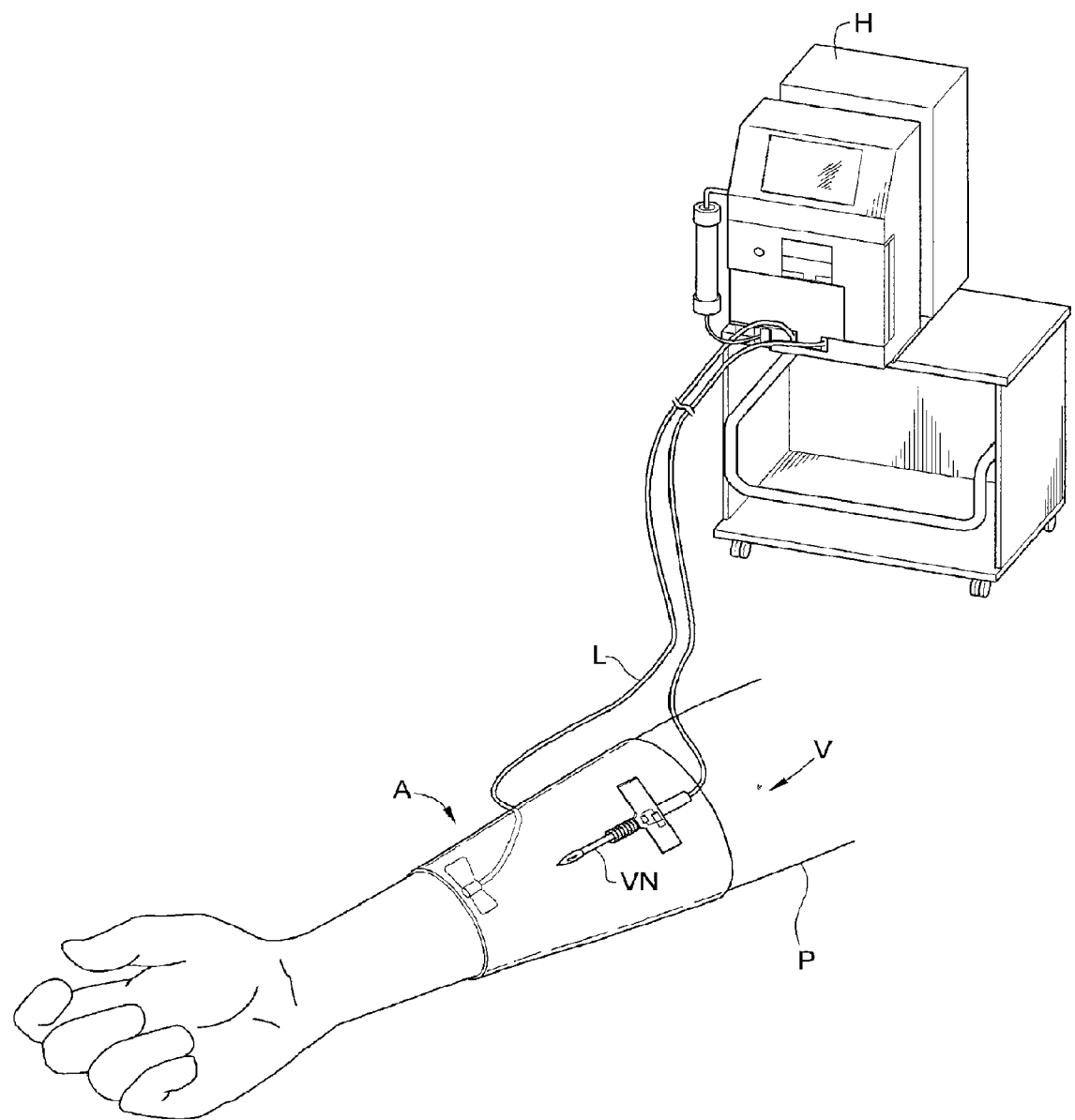
FIG. 1 depicts a prior art access site.
Figure 2:
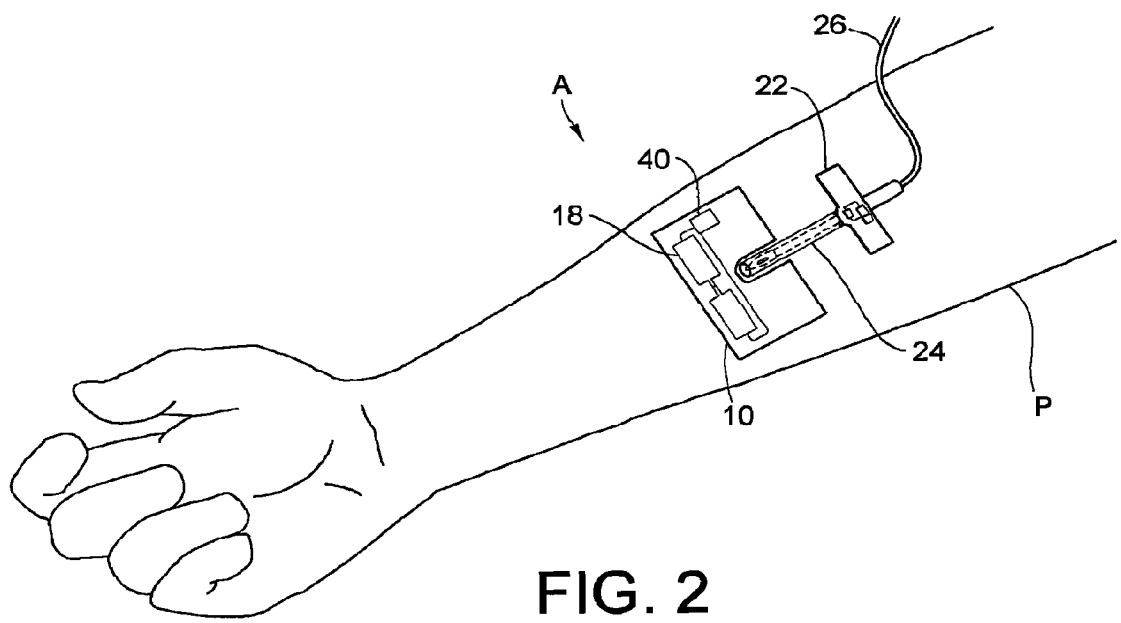
FIGS. 2-3 depicts a first embodiment of an expanding pad with a sensor.
Figure 3:
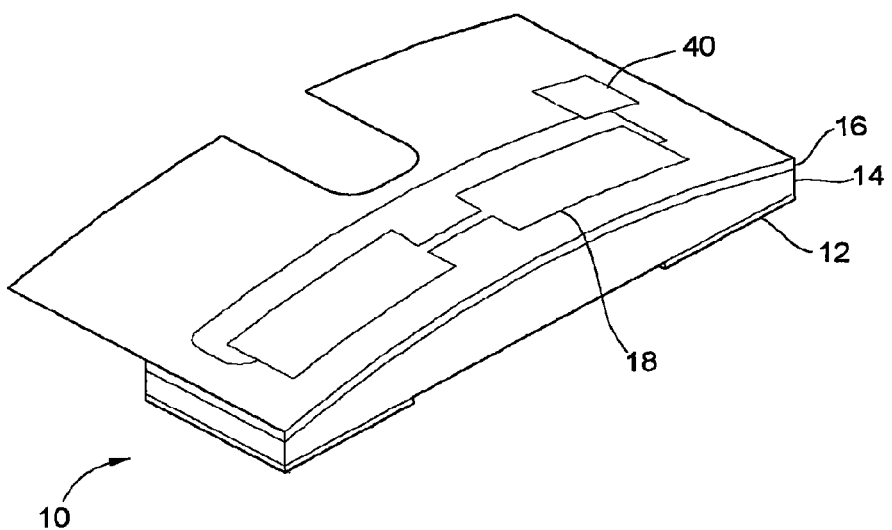

Embodiments of the present invention are useful for monitoring an access site in which a patient receives extracorporeal blood therapy, such as a person undergoing hemodialysis with a hemodialysis machine. An example of such a situation is depicted in FIG. 1, which depicts a patient P undergoing hemodialysis with a hemodialysis machine H. The patient is connected to the hemodialysis machine with tubing lines L connected to an arterial access site A and a venous access site V. Venous access site needle $V_n$ is depicted. Other extracorporeal treatments are also contemplated, such as apheresis.
Expanding Bandage and Sensor Circuit A first embodiment is depicted in FIGS. 2-3. In FIG. 2, a top view of an access site A is depicted, with a bandage 10. The bandage is placed adjacent access site A, so that the bandage is very close to the penetration made by the needle into the arteriovenous fistula commonly used for dialysis in these situations. Venous needle 24 is supported and mounted on the patient by needle mount 22, to which is connected venous tubing 26. The needle mount is typically taped onto the patient to restrain the needle during treatment and keep it reliably in place. The bandage, as seen, includes a continuity sensor 18 and a control circuit 40 atop the bandage. The continuity sensor 18 and control circuit are not limited to the top layer, and indeed may be placed under the top surface of bandage 10, in order to protect sensor.

FIG. 3 depicts a side perspective view of the bandage. The bandage is made from several layers. The first layer 12 is an adhesive to restrain the bandage on the patient. The next layer 14 should also be adjacent the patient. Layer 14 is made from a polymer that expands upon wetting, and especially upon wetting with blood. An optional top layer 16 provides a support for continuity sensor 18. Continuity sensor 18 may be a thin wire, a frangible piece of metal, a thin metallic tape, or any other device useful for maintaining continuity across the top of the bandage during the therapy session. The center portion of layer 14 is made thicker in the center, so that when blood is detected, the expansion of the bandage is non-uniform and is greater in the center, thus causing the continuity sensor 18 to break.

As noted, the expandable or expanding layer is non-uniform, asymmetric, so that upon contact with blood an asymmetric expansion takes place. The asymmetry may be accomplished as shown, with the center portion of the pad thicker, and therefore capable of much greater expansion than the sides. Other configurations may be used, such as layer that expands only on one side, left or right, or front or back, rather than the other side. Still other embodiments could use an inner annular portion with a greater expansion rate than an outer portion, or vice-versa.

The expanding polymer may be one of many polymers that have been developed for this expansion property. Many expanding polymers have been used for medical purposes, such as outlined in U.S. Pat. No. 6,183,436, which discloses uses of such polymers as tampons in body cavities. Among others, materials such as polyvinyl alcohol, reaction products of polyvinyl alcohol and aldehydes, cellulose and cellulose derivatives, polyurethane, and like sponge materials. Another disclosure of such materials is made in U.S. Pat. No. 6,112,380, which discloses many polymers that may be compressed and then are capable of expanding greatly when wetted with water, blood, or other moisture. These materials include starch grafted poly(acrylic acid), a starch derivative, a cellulose derivative, foam, a polymer with a superabsorbent agent (a superabsorbent polymer), poly(vinyl alcohol), poly(alkyl amine), poly(acrylamide) amine derivative, a hydrogel, poly (acrylic acid), microbial cellulose, poly(vinyl pyrrolidone), polyurethane, polyester, polyamide, polyimide, or combinations and/or salts thereof. The collapsible and expandable material is generally very porous. Superabsorbent polymers typically include those made from poly(acrylic acid). Other materials that may be used include poly(ethyleneoxide), poly (caprolactone), and poly(lactic-co-glycolic acid) (PLGA). Any other medically suitable material that has a suitable expansion rate may be used.

As noted above, one of the problems with extracorporeal therapy is dislodgement of the needle, in spite of the care taken during placement. The problem may be more understandable, given the very long nature of some hemodialysis therapy sessions, including overnight sessions in which a patient may move considerably. Thus the need for a detection circuit. In this embodiment, when the needle becomes dislodged, blood will flow from the access site into the bandage, and in particular, into the lowest bandage layer 14, the polymer that expands when wetted. When the polymer expands, and thus layer 14 expands, no provision is made for the expansion of to layer 16 or the continuity sensor 18. Thus, the delicate sensor 18 splits apart upon expansion of layer 14, alerting control circuit 40.

Figure 11:
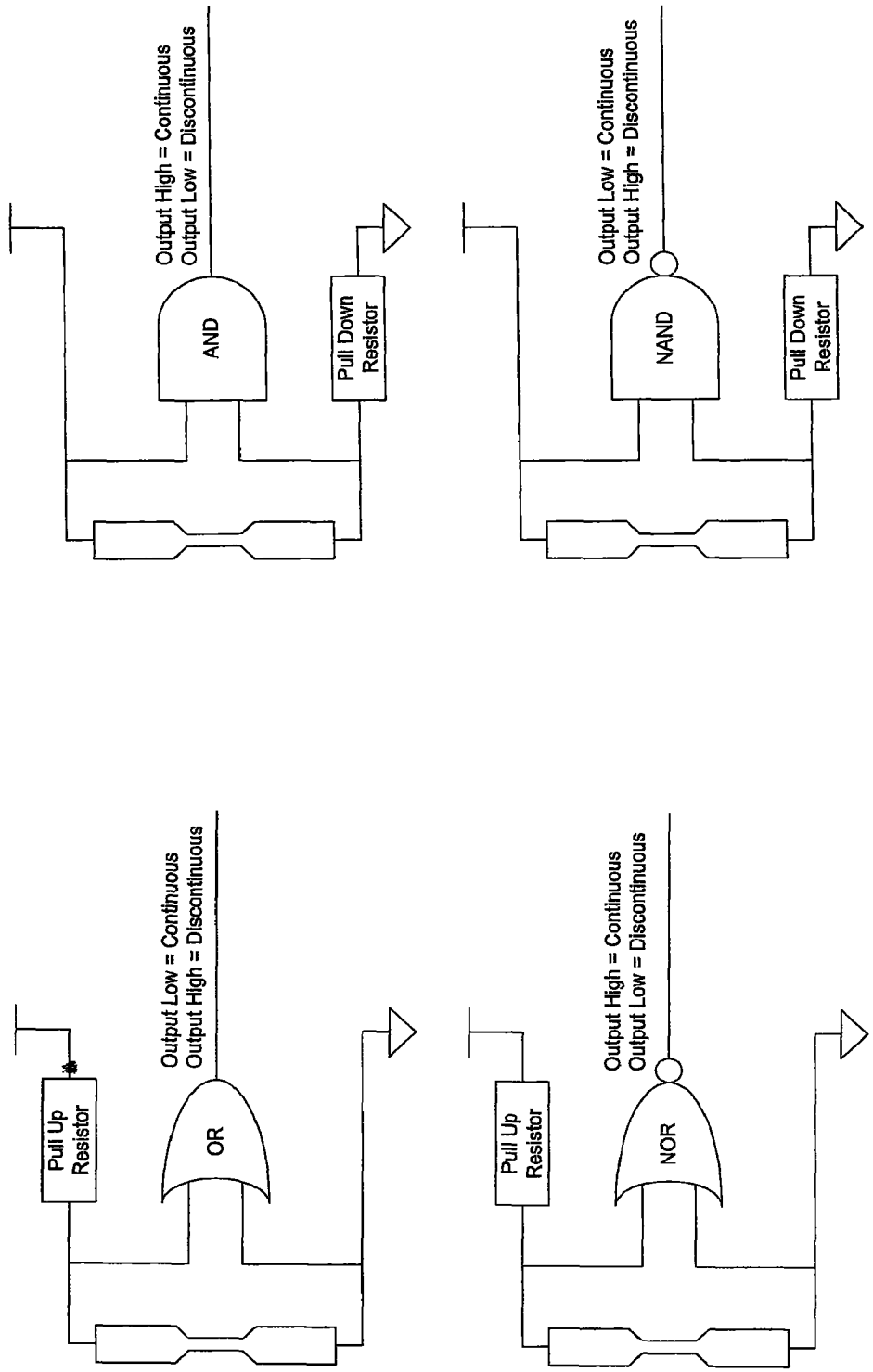
FIG. 11 depicts several simple logic circuits for determining continuity.

Circuit 40 is designed to monitor the health or continuity of sensor 41. control circuit 40 includes a control module 43, which maintains a continuity check on sensor 41, using a voltage check circuit 42, or alternately, a current or resistive reading across the sensor. The control module includes logic such that when there is a change in the continuity of sensor 41, the control module 43 detects the change and the communications module 44 communicates the change. The control circuitry may include a microprocessor to monitor the resistance or voltage drop across sensor 41. Alternately, the control circuitry may simply include an oscillator and timing circuit to periodically check the resistance across the sensor, and using, for example, digital logic, determine when the continuity has been broken and send a signal to that effect via the communications module. Integrated circuits with a simple microcontroller are now sufficiently inexpensive that a very reliable, disposable or single-use circuit can be made with such microcontrollers. However, there are other options, especially with digital circuits, that can also be put into an integrated circuit that does not necessarily require a microcontroller. An example is a suitable combination of AND, NAND, OR and NOR circuits, as depicted in FIG. 11 When the condition of continuity across sensor 41 fails, the logic dictates that a signal be sent to a remote controller to alert the patient or a caregiver of the failure.

The communications module sends signals indicative of its findings or readings to a remote receiver 46. One module that works is a wireless module in accord with ZigBee/IEEE 805.15.4. This is a standard for a very low power radio system with a very limited range, about 10-20 feet. Modules made in accordance with this standard may be purchased from Maxstream, Inc., Lindon, Utah, U.S.A., Helicomm, Inc., Carlsbad, Calif., U.S.A., and ANT, Cochrane, Alberta, Canada. The module is very small, and may be about 2 cm square (about 1 inch square), and about 3 mm thick (⅛ inch). The remote receiver may be part of a therapy machine, or may be a stand-alone circuit for receiving the signals and then alerting the patient or caregiver by with a local output device, such as a speaker 47 or a video screen 48. The monitor may also connect via landline 49, such as to a hospital or clinic information system or other computer or communication system.

Figure 4:
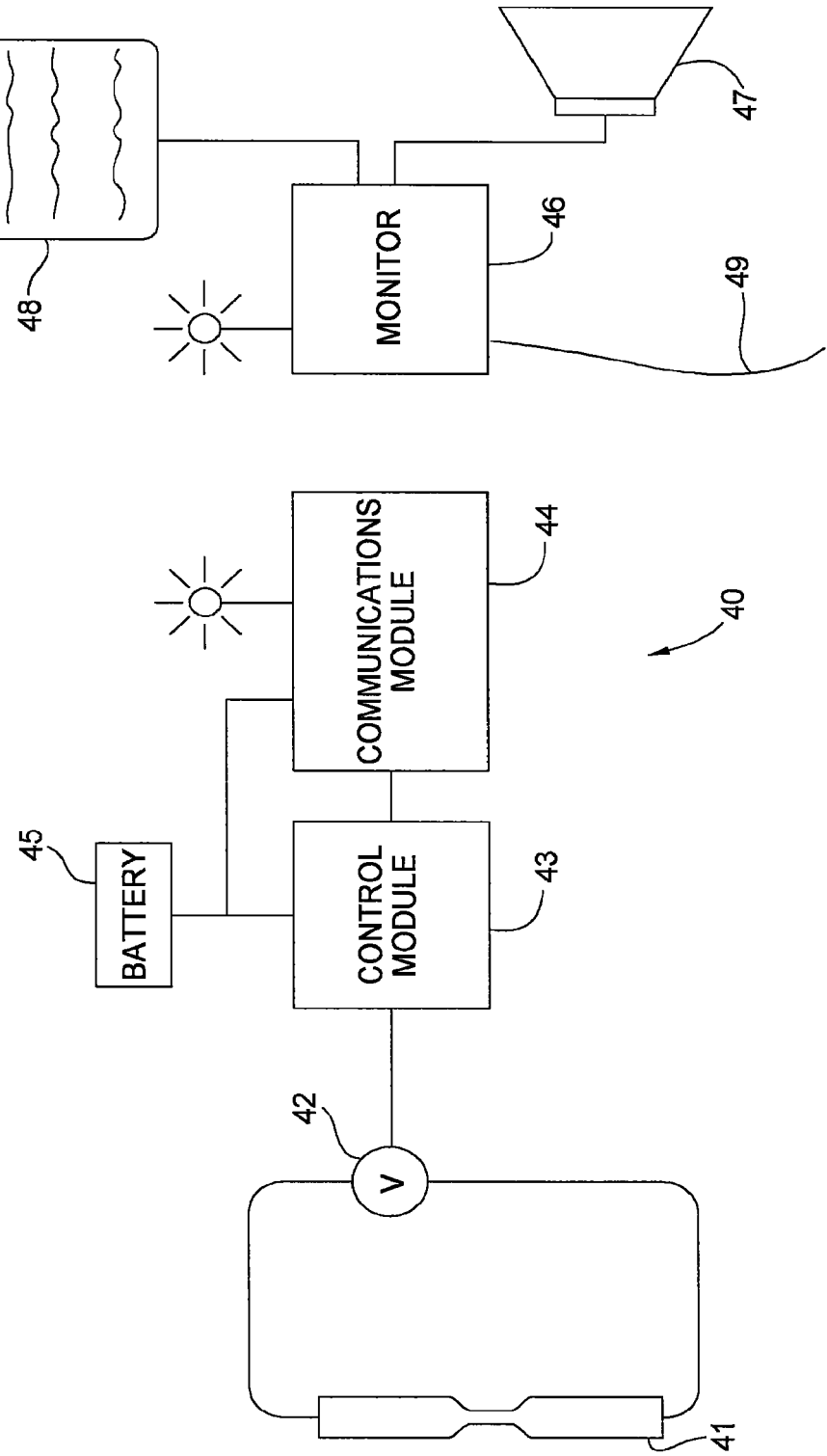
FIG. 4 depicts a circuit for use with the first embodiment.

The control circuitry also includes a battery 45 to power the circuit. The sensor, the control module and the circuitry contained therein, as well as the communications module 44 and a battery 45, are very small so as to fit comfortably atop the bandage. As noted, all the above, except for the battery and the sensor, may be integrated into a microcircuit. The communications module may be wireless as shown in FIG. 4, requiring no harness, cord or cable connection to the patient. Alternately, a cord or cable could be used, which may or may not obviate the need for the battery.

Figure 5:
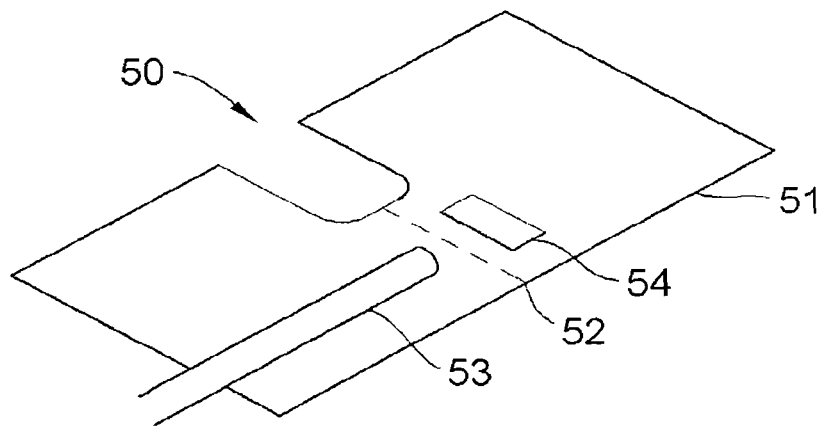
FIG. 5 depicts a second embodiment of an expanding pad with a sensor.

There are many other ways to detect expansion of the expanding polymer. For example, a top view of another sensor pad 50 is depicted in FIG. 5. Sensor pad 50 includes the same construction shown earlier, a first expanding layer intended for placement against the skin of the person near the access site and a barrier layer which may act as a support for detection components atop the pad. In this instance, the top layer 51 of the sensor pad also includes a proximity sensor 53 and a target 54. So long as the sensor detects the target, the pad is presumed to be intact and the access site working properly. If the sensor does not detect the target, it may be because the expanding layer has contacted blood, has expanded, and has caused a split in the sensor pad. The top layer may be provided with a split or a perforation 52 to ease the separation of the sensor from the target in case of an expansion.

Control circuits similar to those already described are used with this embodiment. In this instance, a loss of continuity is not limited to simple electrical conductivity, but also means loss of the detection of the target by the sensor. Proximity sensors include, but are not limited to, capacitance sensors, inductance sensors, hall-effect sensors, and so forth. The target may be any small device that is easily detected by the proximity sensor, such as a small piece of steel, a small magnet, and the like.

Figure 6:
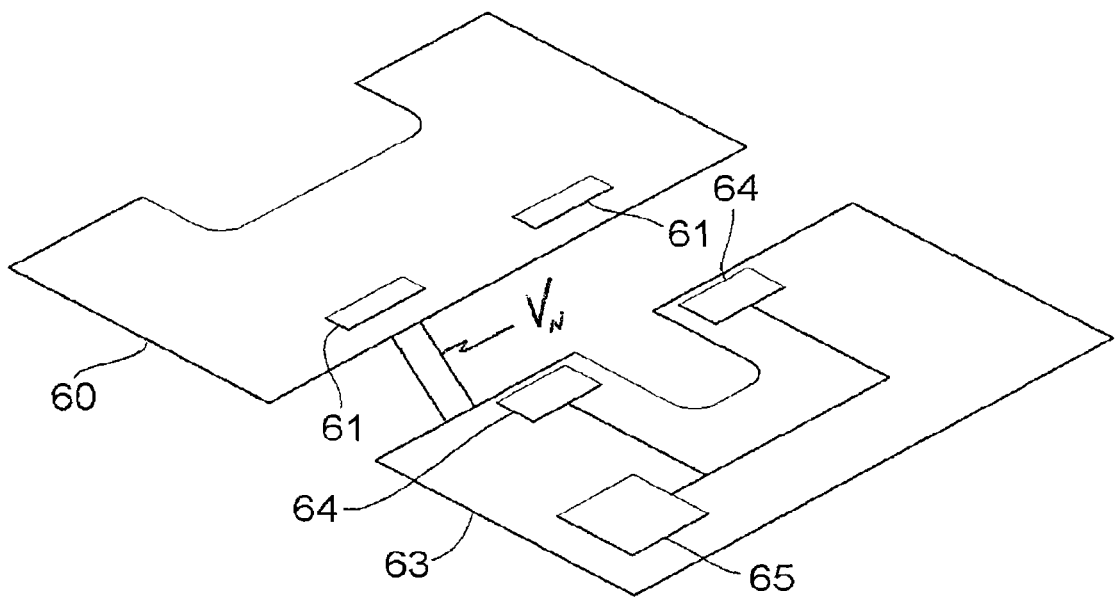
FIG. 6 depicts a third embodiment of an expanding pad with sensors.

Yet another embodiment is disclosed in FIG. 6. In this instance, the needle mount 60 is equipped with two targets 61, on either side of the access needle 66. The sensor pad 63 is constructed as above, but now has two proximity sensors 64 for detecting the targets. Control circuitry 65 may be similar to that described for the previous embodiments, or may be different, so long as the circuitry is capable of detecting the targets and noting and communicating the loss of detection of the targets when the absorbing layer swells and lifts one or both of the proximity sensors 64 out of range of the targets.

The circuitry for the proximity sensors may be set for as sensitive or as rough an adjustment as desired. That is, patients move during long therapy periods. Even though the needle and the pad are firmly taped down, they will still move. Experience with a particular patient, perhaps a very controlled and reliable patient, may show that a 10% change in detection strength is sufficient for dislodgement to have occurred. With a different patient, however, who may be very restless, a 50% change in signal may not indicate that a leak as occurred. The control system is able to accommodate these different situations by accommodating different setups.

Figure 7:
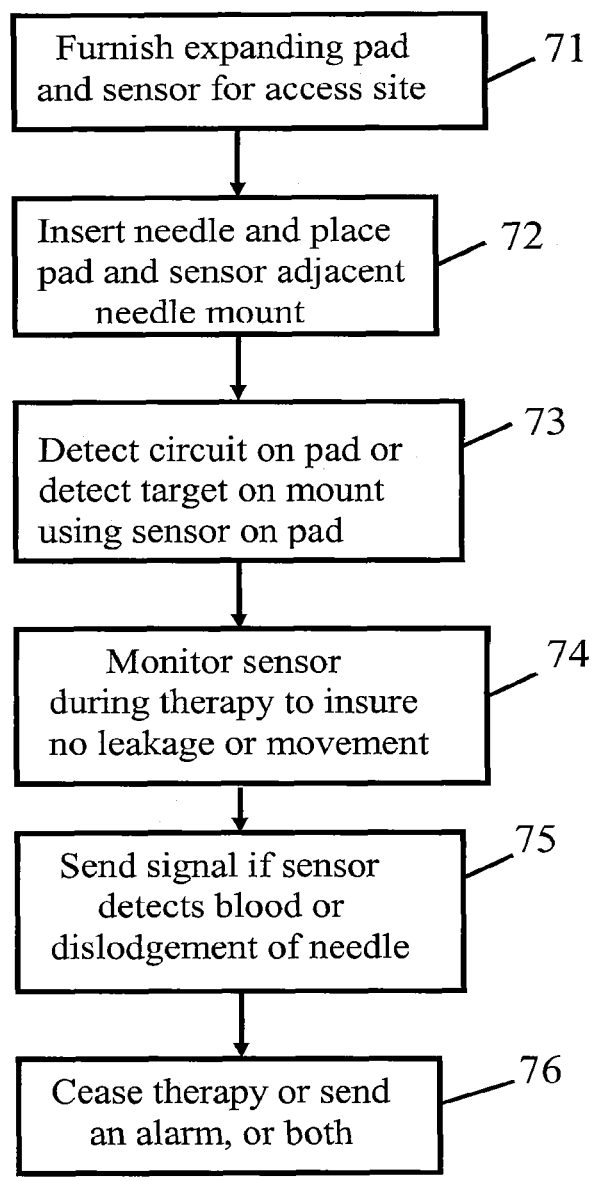
FIG. 7 depicts a method of using an expanding pad to detect leakage of blood at an access site.

One embodiment is a method of using the absorbent pad to detect access disconnection and a blood lead. This embodiment is disclosed in FIG. 7. In one step, an expanding pad with a sensor is furnished 71, the sensor configured for placement near an access site. The access needle is placed into the access site and the sensor is placed 72 adjacent or against the needle mount. The sensor on the pad is detected 73. In alternate embodiments, the sensor detects the target or targets on the needle mount. The sensors are monitored 74 during therapy to insure that a blood leak does not occur, and also, with some embodiments, that needle dislodgement does not occur. If continuity is broken, as in some of the embodiments, or if a sensor no longer detects its target, a signal is sent 75. The signal may cause the therapy machine to shut off, that is, to stop 76 pumping blood from the patient. In other embodiments, the signal is an alert to the patient or caregiver. In other embodiments, an alarm, such as an announcement on a speaker, may be sent.

Rate-Controlled Detection

As noted above, the quickest detection of blood is achieved by an expanding bandage placed directly adjacent the access site. Another aspect of the present invention concerns situations in which the expanding bandage cannot be placed as closely or as conveniently as described above, or a situation in which it is desired to remove the bandage a short distance away, such as 2-5 cm. This situation occurs when the access site has a small amount of blood or other fluid, such as betadene, which would trigger false alarms from other sensors, such the sort of continuity sensors described in U.S. Pat. Nos. 6,445,304 and 6,979,306. In these situations, a minimum amount of fluid, such as blood, is present, often for a period time, before the fluid can present to the sensor. In other situations it may not be possible to place the entire bandage adjacent the site, but it is possible to place a smaller object, such as a sensor inlet tube, into the space available.

Figure 8:
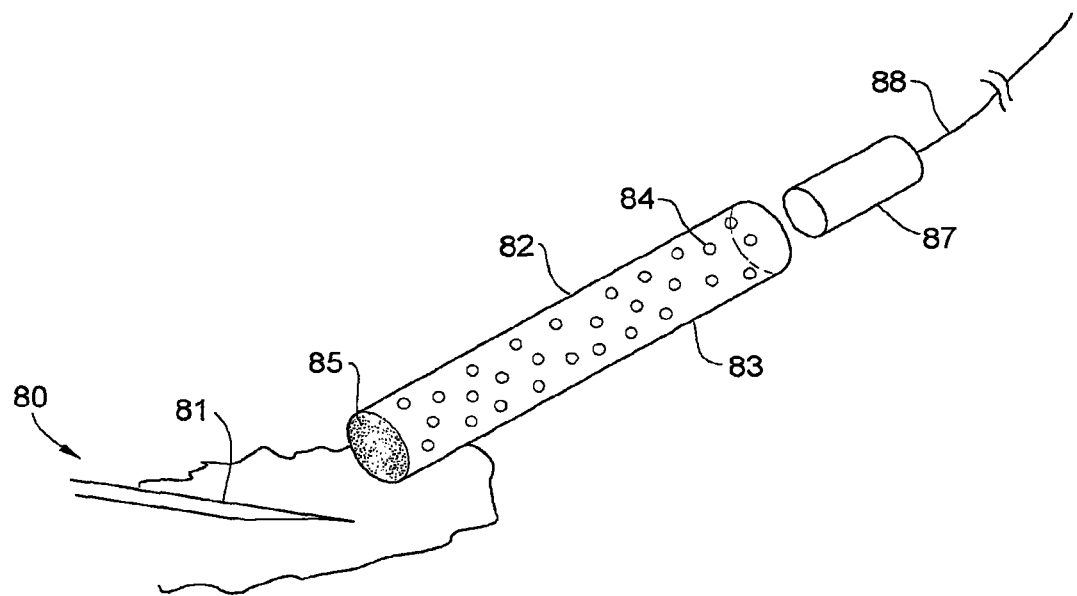
FIG. 8 depicts an additional embodiment, in which a tubular conveyor is placed between an access site and a detector.
Figure 9:
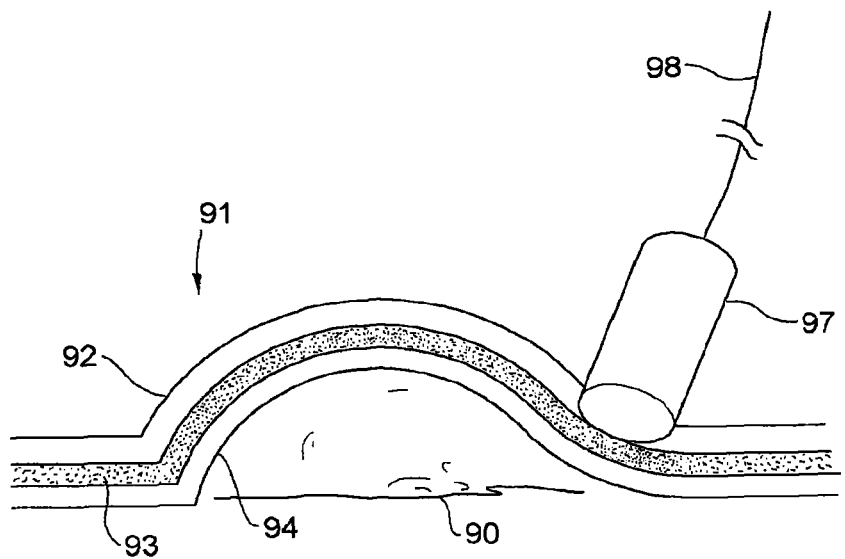
FIG. 9 depicts another embodiment of a pad with a sensor.

This situation is depicted in FIGS. 8 and 9. In FIG. 8, an access site 80 includes a penetrating needle 81, which is preferably not dislodged during treatment or therapy. In the event of dislodgement, however, a distal end of a fluid conveyor 82 has been placed in the limited space available at the access site. Fluid conveyor 82 is connected at its proximal end to a moisture detector 87. Moisture detector 87 may be any suitable moisture detector, such as a capacitance sensor or conductivity circuit. Many such detectors are disclosed in U.S. Pat. No. 7,147,615, assigned to the assignee of the present patent, and which is hereby incorporated by reference in its entirety. As noted above, the conveyor is typically 2-5 cm long, but other lengths may be used, such as 1-10 cm. In one embodiment, the conveyors are manufactured at one length and are trimmed by cutting to the desired length.

Fluid conveyor 82 includes an outer shell 83 with a plurality of apertures 84 through the shell, and also includes an inner packing 85. The outer shell is made from a hydrophobic material, such as polyethylene, polypropylene, FEP (fluorinated ethylenepropylene), or PTFE (polytetrafluoroethylene). These materials will make a durable outer shell or covering. In some embodiments, the conveyor is made in the shape of a collapsed bellows, like some soft-drink straws, so that it is easily formed into a shape for the convenience of the patient. The inner packing 85 is hydrophilic material that is capable of wicking moisture and blood, and conveying the blood from the distal end of the conveyor to the proximal end, where the blood will be detected by the moisture detector 87. Hydrophilic materials include cotton, cellulosics, polyvinyl alcohol (PVA), and polyesters. The packing should be in a form amenable to wicking, such as a foam, a loose packing material, a sponge, or a staple (short fiber) material, such as cotton wool, cotton balls, or other loose, absorbent material. The hydrophobic material on the outside, even when apertures are present, helps to prevent other fluids or materials, such as betadene or other antiseptic, from entering the conveyor, thus restricting use of the conveyor, to the greatest extent possible, for the fluid of interest, typically blood.

If a needle dislodgement occurs, blood will leak onto the access site area and will be absorbed by the fluid conveyor 82 and wicked through the inner packing 85. The wicking will transport the blood through the conveyor until the blood is detected by moisture sensor 87. The moisture sensor, a conductive, capacitive, or other moisture sensor, will send a signal via its connecting lines 88 to a controller or other remote device to alert the user that blood has been detected. In other embodiments, sensor 87 may be part of a wireless circuit for monitoring the patient during the therapy procedure, such as the monitor and circuit depicted in FIG. 4. The wicking process will take longer than if sensor 87 were directly mounted near the access site. This is desirable in the situations described above in which a part of the capacity of the conveyor has already been used for small amounts of blood that were present at the access site when hemodialysis began. This small delay is thus desirable to prevent false alarms.

In order for fluid conveyor 82 to work properly, the blood that passes through the conveyor should not clot. This can be arranged by adding anti-coagulant to the packing material. Examples of anti-coagulant material include heparin, acid and citrate dextrose (ACD). The amount of anti-coagulant needed depends on the packing material, the length of the therapy, the evaporation rate of the anti-coagulant, the temperature of the conveyor, and many other variables. Other anti-coagulants can be used, such as any medication with acceptable use as a blood thinner that will not be applied to the vascular system of the patient.

Another situation using a patch 91 with hydrophilic and hydrophobic components is depicted in FIG. 9. This embodiment is also useful in preventing false alarms Patch 91 is placed over access site 90 to protect and monitor the site and to insure that no leakage or access disconnect occurs, while allowing for the presence of very small amounts blood or fluid in a quiescent or non-accumulating manner. The patch includes a top layer 92 of hydrophobic material, to keep moisture away from entering the site. Middle layer 93 includes a hydrophilic filler, as discussed above, to wick moisture from the source to the sensor 97, no matter where on or in the patch the sensor is located. Bottom layer 94 is porous, i.e., includes a plurality of apertures for admitting moisture or blood for detection by sensor 97. Bottom layer 97 is also made from a hydrophobic material. Sensor 97 is connected to a remote monitor or control circuit by cable 98, wherein remote may mean as little as a few feet or a meter away. When blood is detected by the sensor, the sensor control circuit detects the change in the sensor reading and takes appropriate action, such as to alert a user or a caregiver. In other embodiments, sensor 97 may be part of a wireless circuit for monitoring the patient. An example is the monitor and control circuit depicted in FIG. 4.

Dissolving Insulator

Figure 10:
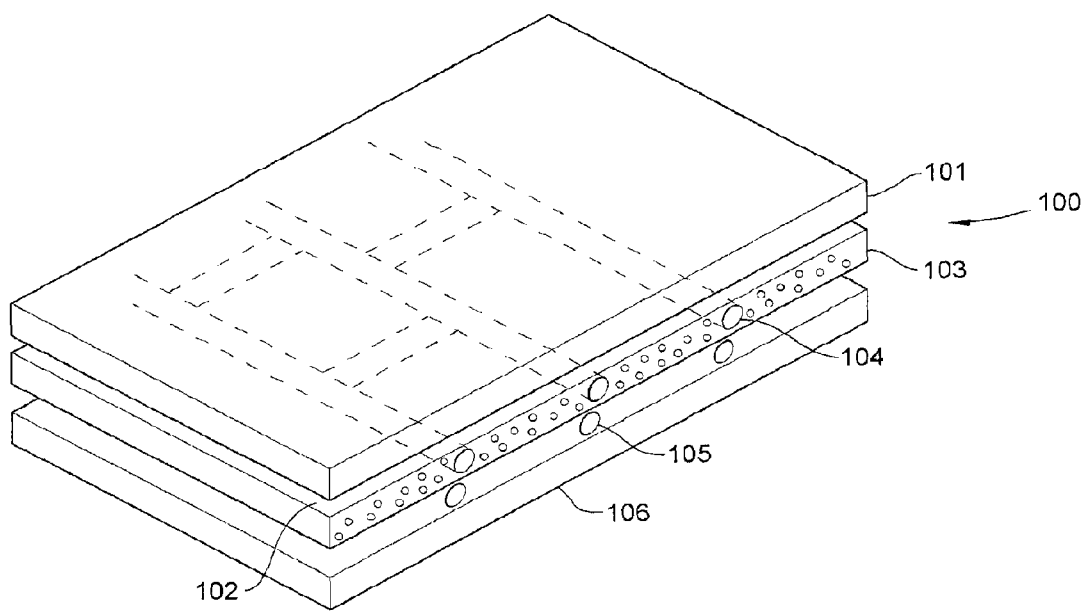
FIG. 10 depicts a another embodiment of a pad with a continuity sensor.
Figure 10:
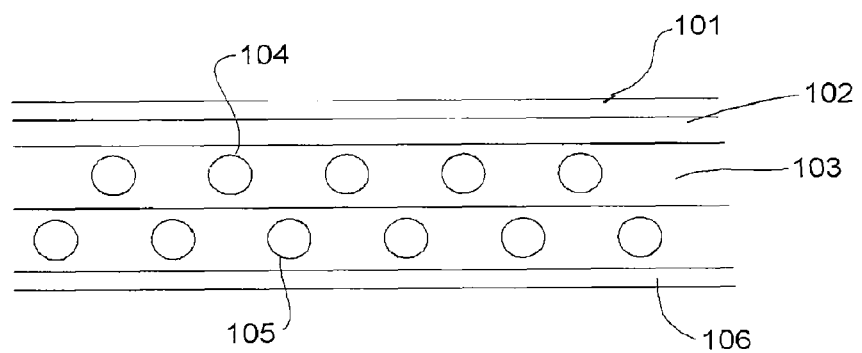

In another embodiment, connecting wires in a continuity circuit are held apart by a polymer that dissolves when contacted by blood. Another embodiment uses a multi-layer pad 100 with a continuity detector, as shown in FIG. 10. This embodiment includes a top layer 101, which may be any medically acceptable cover, such as polyethylene, nylon, cotton, and the like. To top layer 101 is adhered a middle layer 103 in which are embedded one or more electrically-conductive wires 104, forming an interconnected wire network. Wires 104 are desirably connected electrically so that when one of the wires 104 touches a wire in the second network of electrically-conductive wire network 105 beneath middle layer 103, the two networks are electrically connected. Below second network 105 is a bottom cover layer 106.

The first wire network 104 is embedded within a material that dissolves when it wets blood. There are many examples of such materials, as disclosed in U.S. Pat. Nos. 4,501,828, 4,499,214, and 5,332,524, each of which is hereby incorporated by reference, as though each page and figure were set forth explicitly herein. These documents teach numerous polymer materials that may be prepared and which dissolve upon contact with water. These materials include polyethylene oxide, polyacrylamide, polysaccharides (which may be sugars), and salts of these materials. These materials have also been found to dissolve upon contact with water, and they will also dissolve on contact with blood.

The wire is prepared and the dissolving polymers are formed around the wires to form insulated-wire layer 103. A second layer of wires 105 is prepared and is placed adjacent the insulated-wire layer 103. The polymer insulation prevents contact between the wires of layers 103 and 105. Bottom layer 106 insulates the second layer of wires 103 and protects the wires from inadvertent contact. In one embodiment, a pressure-sensitive adhesive 102 is used to removably adhere cover 101 to the insulated wire layer.

In use, the top layer 101 may be peeled away from insulated wire layer 103, and the insulated wire layer placed near the access site, with the pad secured by adhesive tape and with layer 106 facing away from the patient. If an access disconnect occurs, or if the site leaks blood, the blood will dissolve the dissolving polymer and one or more of the wires 104 will contact one or more of wires 105, thus completing a connection between the two sets. Circuits such as those described above may be used to monitor the conductivity or resistance between the two sets of wires. As one example, bundles of very small Litz wire may be used.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. An access disconnect system comprising:
   an extracorporeal therapy machine; and
   an access disconnect detector operable with the extracorporeal therapy machine, the access disconnect detector including:
   a first layer including a dissolving polymer and a first electrically conductive wire network embedded in the first layer; and a second layer including a second electrically conductive wire network embedded in the second layer, wherein the access disconnect detector is configured (i) for placement near or atop a patient access site for an extracorporeal therapy, and (ii) such that when blood contacts the dissolving polymer, the polymer dissolves sufficiently so that at least one wire of the first electrically conductive wire network contacts at least one wire of the second electrically conductive wire network so as to complete an electrical circuit.

2. The access disconnect system of claim 1, which includes a cover layer removably adhered to the first layer.

3. The access disconnect system of claim 1, wherein the second at least one conductor includes a plurality of conductors, and which includes a cover layer positioned over the second layer, the cover layer configured to electrically insulate the plurality of conductors from each other.

4. The access disconnect system of claim 1, which includes a control circuit, wherein the control circuit is configured to send an alert signal indicative of a presence of blood upon the completion of the electrical circuit.

5. The access disconnect system of claim 1, wherein the access disconnect detector is configured for wireless communication with the extracorporeal therapy machine or a controller in communication with the extracorporeal therapy machine.

6. The access disconnect system of claim 1, wherein the dissolving polymer is selected from the group consisting of polyacrylamides, polysaccharides and salts thereof.

7. The access disconnect of claim 1, wherein the access disconnect detector is configured such that when blood contacts the dissolving polymer, the polymer dissolves sufficiently so that a plurality of wires of the first electrically conductive wire network contacts a plurality of wires of the second electrically conductive wire network to complete the electrical circuit.

8. An access disconnect system comprising:
an extracorporeal therapy machine; and
an access disconnect detector operable with the extracorporeal therapy machine, the access disconnect detector including:
a dissolving polymer layer including a first electrically conductive wire network embedded in the dissolving polymer layer, and
a second layer including a second electrically conductive wire network embedded in the second layer,
wherein the system is configured such that (i) the access disconnect detector can be placed near or atop a patient access site for an extracorporeal therapy, and (ii) when blood contacts the dissolving polymer layer, the polymer dissolves sufficiently so that at least one wire of the first electrically conductive wire network contacts at least one wire of the second electrically conductive wire network to complete an electrical circuit.

9. The access disconnect system of claim 8, wherein the access disconnect sensor includes a cover layer adhesively secured to the dissolving polymer layer.

10. The access disconnect system of claim 8, wherein the access disconnect detector is configured to communicate wirelessly with the extracorporeal therapy machine.

11. The access disconnect system of claim 8, which includes a remote receiver in communication with the access disconnect detector, wherein the access disconnect detector is configured to send a signal indicative of a presence of blood to the remote receiver upon the completion of the electrical circuit.

12. The access disconnect system of claim 8, which includes a removable cover positioned over the second layer to electrically insulate the first at least one conductor.

13. The access disconnect system of claim 8, which includes a remote receiver and a control circuit, wherein (i) the access disconnect detector electrically communicates with the control circuit to generate a signal upon completion of the electrical circuit, and (ii) the remote receiver is configured to receive the signal from the control circuit.

14. The access disconnect system of claim 8, wherein the second electrically conductive wire network includes a plurality of conductors, and which includes a cover layer positioned over the second layer, the cover layer configured to electrically insulate the plurality of conductors from each other.

15. The access disconnect system of claim 8, wherein the dissolving polymer layer includes a polymer selected from the group consisting of polyacrylamides, polysaccharides and salts thereof.

16. An access disconnect method comprising:
enabling an access disconnect detector to be placed atop or near a patient access site for an extracorporeal therapy, the access disconnect detector having a polymer layer and a second layer; and
configuring the polymer layer to dissolve upon contact with blood such that at least one wire of a first electrically conductive wire network embedded in the polymer layer contacts at least one wire of a second electrically conductive wire network embedded in the second layer to complete an electrical circuit.

17. The access disconnect method of claim 16, which includes configuring the access disconnect detector to be placed atop or near the patient access site.

18. The access disconnect method of claim 16, which includes configuring the access disconnect detector to be secured the patient access site so that the polymer layer contacts the patient access site.

19. The access disconnect method of claim 16, which includes electrically insulating the second layer from the polymer layer.

20. The access disconnect method of claim 16, which includes sending a blood alert signal upon the completion of the electrical circuit.

* * * * *